(12) United States Patent
Leal et al.

(10) Patent No.: US 9,171,369 B2
(45) Date of Patent: Oct. 27, 2015

(54) COMPUTER-AIDED DETECTION (CAD) SYSTEM FOR PERSONALIZED DISEASE DETECTION, ASSESSMENT, AND TRACKING, IN MEDICAL IMAGING BASED ON USER SELECTABLE CRITERIA

(75) Inventors: Jeffrey Leal, Baltimore, MD (US); Richard L. Wahl, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 146 days.

(21) Appl. No.: 13/880,587

(22) PCT Filed: Oct. 26, 2011

(86) PCT No.: PCT/US2011/057890
§ 371 (c)(1),
(2), (4) Date: Apr. 19, 2013

(87) PCT Pub. No.: WO2012/058310
PCT Pub. Date: May 3, 2012

(65) Prior Publication Data
US 2013/0208963 A1 Aug. 15, 2013

Related U.S. Application Data

(60) Provisional application No. 61/406,693, filed on Oct. 26, 2010, provisional application No. 61/453,647, filed on Mar. 17, 2011.

(51) Int. Cl.
*G06T 7/00* (2006.01)
*A61B 6/00* (2006.01)
*G06F 19/00* (2011.01)

(52) U.S. Cl.
CPC ............ *G06T 7/0014* (2013.01); *A61B 6/5217* (2013.01); *G06F 19/3487* (2013.01);
(Continued)

(58) Field of Classification Search
None
See application file for complete search history.

(56) References Cited

U.S. PATENT DOCUMENTS 6,195,409 B1 * 2/2001 Chang et al. .................... 378/20
6,366,797 B1 * 4/2002 Fisher et al. .................. 600/410
(Continued)

FOREIGN PATENT DOCUMENTS

WO WO-2009/058915 A1 5/2009

OTHER PUBLICATIONS

Hahn, S. et al, "Computer-Aided Detection (CAD) and Assessment of Malignant Lesions in the Liver and Lung using a Novel PET/CT Software Tool: Initial Results," 182(3) Rofo-Fortschritte Auf Dem Gebiet Der Rontgenstrahlen Und Der Bildgebenden Verfahren 243, Mar. 2010.
(Continued)

*Primary Examiner* — Tsung-Yin Tsai
(74) *Attorney, Agent, or Firm* — Venable LLP; Henry J. Daley

(57) ABSTRACT

An embodiment of the current invention includes computer-implemented method for image processing. The method includes receiving a first medical image from a data storage device, the first medical image comprising a plurality of image voxels and representing a plurality of tissue regions of a subject; automatically determining a reference value based on the first medical image, the reference value capable of providing a range of background level of voxel intensity values within at least one non-disease tissue region of the subject; generating a disease threshold based on the reference value; identifying portions of the medical image corresponding to disease-tissue regions according to the disease threshold, each of the portions comprising a plurality of connected image voxels in the medical image; and entering data encoding the disease-tissue regions into a database for subsequent comparisons.

17 Claims, 11 Drawing Sheets

(52) U.S. Cl.
CPC ........... *A61B2576/00* (2013.01); *G06F 19/321* (2013.01); *G06T 2207/10072* (2013.01); *G06T 2207/30016* (2013.01); *G06T 2207/30096* (2013.01)

(56) References Cited

U.S. PATENT DOCUMENTS

| | | | |
|---|---|---|---|
| 6,430,430 B1* | 8/2002 | Gosche | 600/410 |
| 2005/0065432 A1* | 3/2005 | Kimura | 600/420 |
| 2005/0165294 A1* | 7/2005 | Weiss | 600/410 |
| 2007/0081706 A1* | 4/2007 | Zhou et al. | 382/128 |
| 2007/0081712 A1 | 4/2007 | Huang et al. | |
| 2008/0249396 A1 | 10/2008 | Biglieri et al. | |
| 2009/0129641 A1 | 5/2009 | Zhou | |
| 2010/0049035 A1* | 2/2010 | Hu et al. | 600/425 |
| 2010/0067761 A1* | 3/2010 | Jakobsson et al. | 382/131 |

OTHER PUBLICATIONS

Kortesniemi, M. et al., "Automatic Image Quality Quantification and Mapping with an Edge-Preserving Mask-Filtering Algorithm," Acta Radiologica 49(1) 45, 2008.

Levy, R., "A Histogram-Based Algorithm for Semiautomated Three-Dimensional Craniofacial Modeling," Academic Radiology 2(7) 592, Jul. 1995.

International Search Report and Written Opinion of PCT/US2011/057890.

* cited by examiner

| Standard Disease Threshold Algorithm (1.5 Liver_mean) + (2 Liver_SD) | | | |
|---|---|---|---|
| | # Detected Cases | % of N(=29) | CAD as % of Expert |
| Expert Reader – PEAK | 25 | 86% | |
| Expert Reader – MAX | 26 | 90% | |
| CAD – PEAK detector | 24 | 83% | 96% |
| CAD – MAX detector | 27 | 93% | 104% |

FIG. 4A

| TLG Disease Threshold Algorithm (10 Liver$_{mean}$) + (2 Liver$_{sd}$) | | | |
|---|---|---|---|
| | # Detected Cases | % of N(=29) | CAD as % of Expert |
| Expert Reader – PEAK | 27 | 93% | |
| Expert Reader – MAX | 29 | 100% | |
| CAD – PEAK detector | 27 | 93% | 100% |
| CAD – MAX detector | 28 | 97% | 97% |

FIG. 4B

| Lesion Detectability Standard vs TLC Disease Threshold | | | |
|---|---|---|---|
| | # Detected Cases Standard Threshold | # Detected Cases Alternative Threshold | % Difference (Alt vs Std Threshold) |
| Expert Reader – PEAK | 25 | 27 | 8% |
| Expert Reader – MAX | 26 | 29 | 12% |
| CAD – PEAK detector | 24 | 27 | 13% |
| CAD – MAX detector | 27 | 28 | 4% |

FIG. 4C

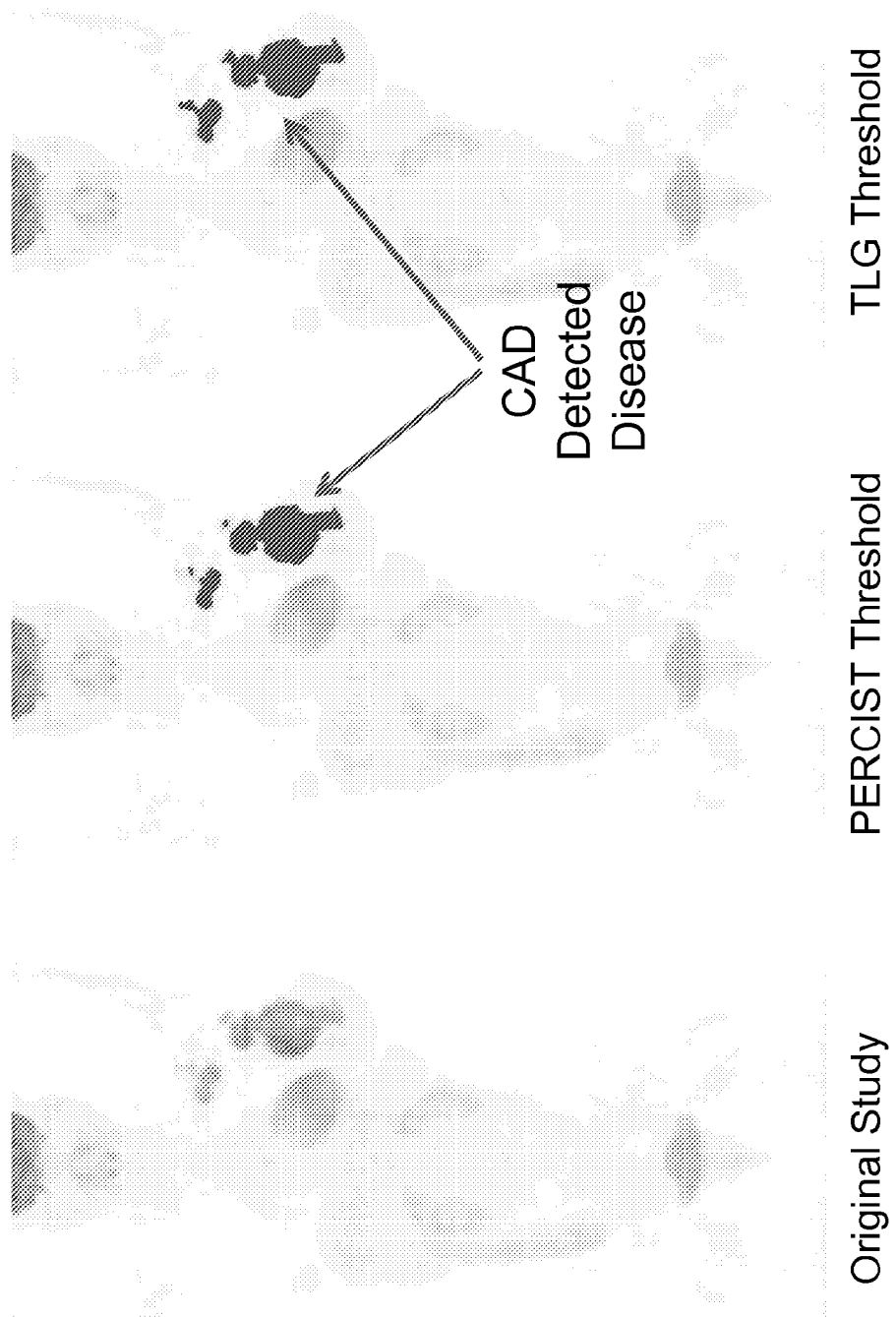

COMPUTER-AIDED DETECTION (CAD) SYSTEM FOR PERSONALIZED DISEASE DETECTION, ASSESSMENT, AND TRACKING, IN MEDICAL IMAGING BASED ON USER SELECTABLE CRITERIA

CROSS-REFERENCE OF RELATED APPLICATION

This application claims priority to U.S. Provisional Application No. 61/406,693 filed on Oct. 26, 2010, and U.S. Provisional Application No. 61/453,647 filed on Mar. 17, 2011, the entire contents of both provisional applications are hereby incorporated by reference, and is a U.S. National Stage Application under 35 U.S.C. §371 of PCT/US2011/057890, filed Oct. 26, 2011, the entire contents of which are incorporated herein by reference.

BACKGROUND

1. Field of Invention

The current patent application generally relates to medical image processing.

2. Discussion of Related Art

The ultimate goal of new cancer therapies is cure. A good cancer treatment should ideally prolong survival while preserving a high quality of life cost-effectively. To demonstrate prolonged survival in a clinical trial in some more slowly progressing cancers can take 5-10 years or longer. Such trials are expensive, not only in cost but in time.

The typical development pathway for cancer therapeutic drugs includes an evolution from phase I to phase II and to phase III clinical trials. In phase I trials, toxicity of the agent is typically assessed to determine what dose is appropriate for subsequent trials. Typically, the statistical power of phase I drug trials is inadequate to assess antitumor efficacy. In phase II trials, evidence of antitumor activity is obtained. Phase II trials can be done in several ways. One approach is to examine tumor response rate versus a historical control population treated with an established drug. New drugs with a low response rate are typically not moved forward to advanced clinical testing under such a paradigm. In such trials, tumor response has nearly always been determined anatomically. An alternative approach is to use a typically larger sample size and have a randomized phase II trial, in which the new treatment is given in one treatment arm and compared with a standard treatment. Once drug activity is shown—or suggested—in phase II, phase III trials are typically performed. Phase III trials are larger and typically have a control arm treated with a standard therapy. Not all phase III trials are successful, but all are costly.

Determining which innovative cancer therapeutics should be advanced to pivotal large phase III trials can be unacceptably delayed if survival is the sole endpoint for efficacy. Survival trials can also be complicated by deaths due to non-malignant causes, especially in older patients in whom comorbidities are common. Additional complexities can include patients who progress on a clinical trial but who go on to have one of several nonrandomly distributed follow-up therapies—which can confound survival outcomes.

Therefore, there is great interest in surrogate metrics for survival after investigational cancer treatments, such as response rate, time to tumor progression, or progression-free survival. Changes in tumor size after treatment are often, but not invariably, related to duration of survival. To this end, a variety of approaches to measuring response rate have been developed, beginning with the original reports by Moertel on physical examination in 1976 and continuing to the subsequent World Health Organization (WHO) criteria (1979), Response Evaluation Criteria in Solid Tumors (RECIST) (2000), and RECIST 1.1 (2009). These approaches typically focus on how often a tumor shrinks anatomically and defined such response in several ways, including, for example. complete response, partial response, stable disease, and progressive disease. This type of classification divides intrinsically continuous data (tumor size) into 4 bins, losing statistical power for ease of nomenclature and convenience.

Thus, intrinsic limitations of currently applied anatomic tumor response metrics, including WHO, RECIST, and the new RECIST 1.1 criteria, led to on-going pursuit for quantitative and qualitative approaches to investigate surrogate endpoints based on functional imaging such as Positron Emission Tomography/Computed Tomography (PET/CT). In particular, a framework for PET Response Criteria in Solid Tumors (PERCIST, version 1.0) has been recently proposed. These functional surrogate endpoints may be useful in future multicenter trials and may serve as a starting point for further refinements of quantitative PET response. They may also provide some guidance for clinical quantitative structured reporting on individual patients. Thus, there is a need in the art for a method that can be objectively implemented by different users in a multi-center environment to monitor a patient's condition over time (i.e., in a longitudinal manner).

SUMMARY

An embodiment of the current invention includes a computer-implemented method for image processing, the method comprising receiving a first medical image from a data storage device, the first medical image comprising a plurality of image voxels and representing a plurality of tissue regions of a subject; automatically determining a reference value based on the first medical image, the reference value capable of providing a range of background level of voxel intensity values within at least one non-disease tissue region of the subject; generating a disease threshold based on the reference value; identifying portions of the medical image corresponding to disease tissue regions according to the disease threshold, each of the portions comprising a plurality of connected image voxels in the medical image; and entering data encoding the disease tissue regions into a database for subsequent comparisons.

BRIEF DESCRIPTION OF THE DRAWINGS

Further objectives and advantages will become apparent from a consideration of the description, drawings, and examples.

FIG. 4A tabulates the summary outcome from the expert and automated detection using the standard disease threshold algorithm according to some embodiments of the current invention.

FIG. 4B tabulates the summary outcome from the expert and automated detection using the TLG disease threshold algorithm according to some embodiments of the current invention.

FIG. 4C compares the summary outcome from the expert and automated detection using the standard and TLG disease threshold algorithms according to some embodiments of the current invention.

FIG. 5A shows an example detection of disease region in one original medical image of using the standard and the TLG disease thresholds determined according to some embodiments of the current invention.

DETAILED DESCRIPTION

Some embodiments of the current invention are discussed in detail below. In describing the embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Figure 1A:
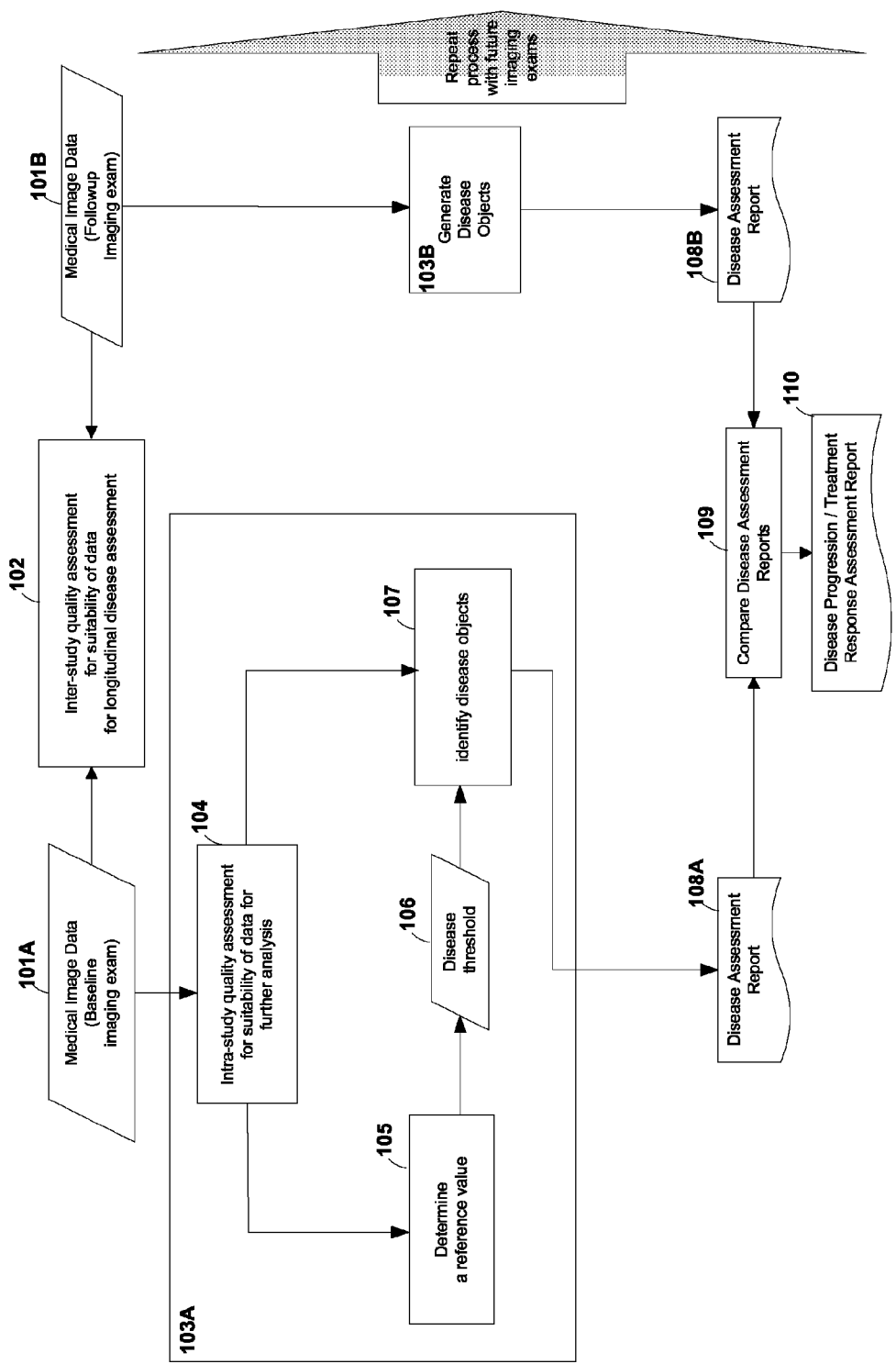
FIG. 1A shows a flow-chart according to an embodiment of the current invention.

FIG. 1A shows a flow-chart according to an embodiment of the current invention. Blocks 101A and 101B may represent medical image data over a time course of a subject under observation. The subject may be a human patient, an animal, etc. For example, block 101A may represent the medical image of a human patient with an abnormality before treatment. The medical image may comprise a plurality of image voxels and may represent multiple tissue regions of the subject. The medical image may include, for example, a Positron Emission Tomography/Computed Tomography (PET/CT) image, a Magnetic Resonance Imaging (MRI) image, etc. The medical image of block 101A may be taken from a baseline imaging exam before commencement of treatment. The abnormality may be a tumor a tumor, a neoplasia, a hyperplasta, or a dysplasia. The cancer treatment may include, for example, radiation therapy, chemotherapy, high-intensity focused ultrasound (HIFU) therapy, radio-frequency (RF) ablation therapy, laser ablation therapy, oral-dose treatment, or combinations thereof. The abnormality may also be a neurodegenerative disorder, such as, for example, Alzheimer's disease, Parkinson's disease, Wilson's disease, or a dementia precursor condition. The corresponding treatment may include, for example, oral-dose treatment. The medical image of block 101A may be taken from a follow-up exam of the same subject, for example, after commencement of treatment. Block 102 represents inter-study quality assessment to determine the suitability of data of block 101A and 101B for a longitudinal (i.e., over a time course) study.

Block 103A generates a disease assessment report 108A based on baseline medical image of 101A. Block 104 performs a quality assessment on the baseline medical image from block 101A to ascertain the quality suitability for subsequent analysis. A quality assessment may include, for example, checking for consistency in image protocol between imaging sessions, camera usage, etc. In block 105, a reference value is automatically determined based on the medical image of block 101A. The reference value is capable of providing a range of background level of voxel intensity values within at least one non-disease tissue region of the subject. A disease threshold 106 may be determined based on the reference value. In block 107, portions of the medical image of 101A corresponding to disease tissue regions can then be identified according to the disease threshold of block 106. Each of the portions comprising a plurality of connected image voxels in the medical image of block 101A. Thereafter, data encoding said disease tissue regions may be entered into a database, in the form of a disease assessment report for subsequent comparisons.

Similarly, Block 103B generates a disease assessment report 108B based on baseline medical image of 101B. This procedure may be repeated for later imaging exams as indicated in FIG. 1A.

Figure 1B:
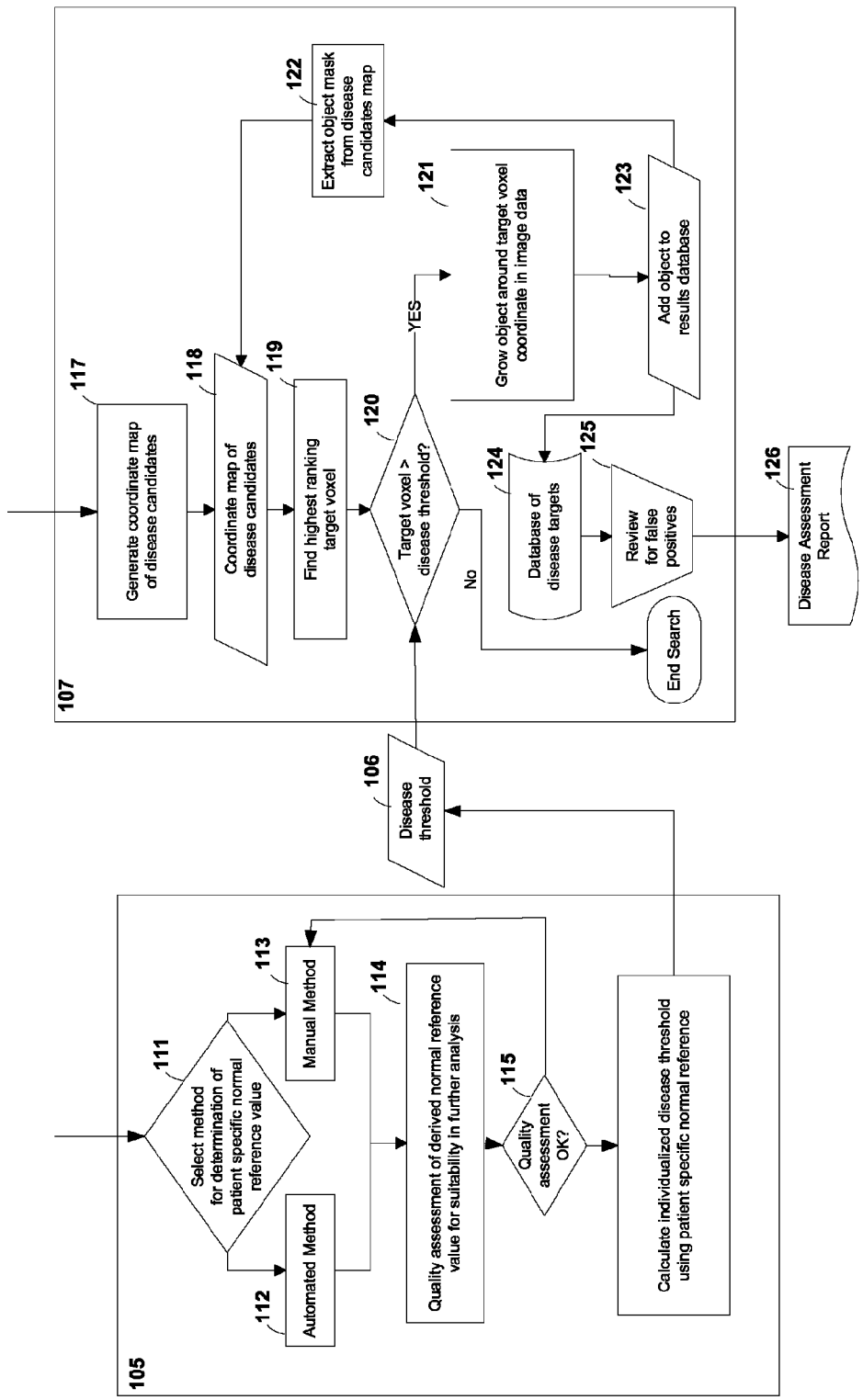
FIG. 1B shows detailed flow charts of blocks 105 and 107 of FIG. 1A according to some embodiments of the current invention.
Figure 1C:
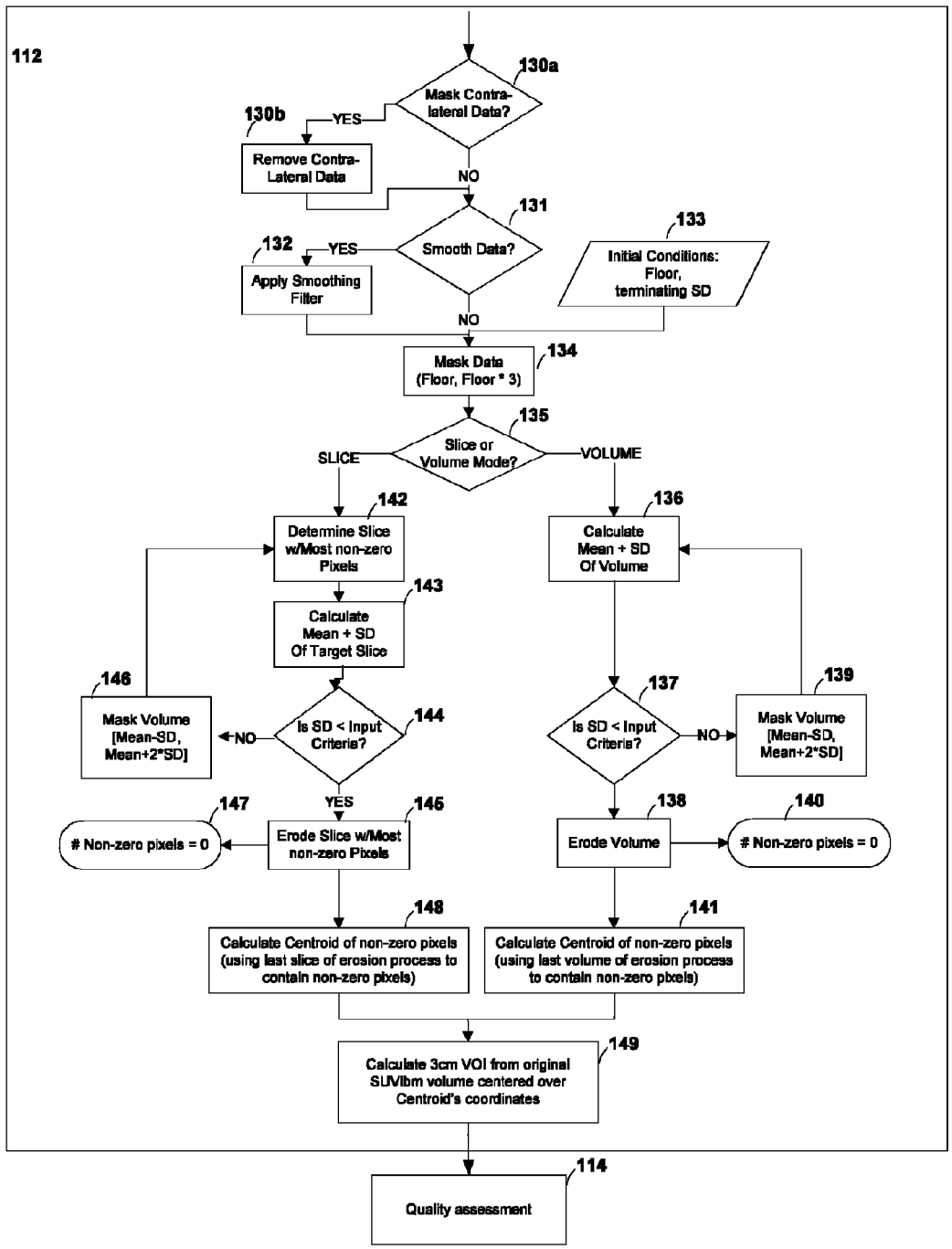
FIG. 1C shows detailed flow charts of blocks 112 FIG. 1B according to some embodiments of the current invention.

FIG. 1B shows detailed flow charts of blocks 105 and 107 of FIG. 1A according to some embodiments of the current invention. In block 105, a selection is made in block 111 to either use automated method 112 or manual method 113 to generate the reference value. FIG. 1C shows detailed flow charts of block 112 of FIG. 1B according to some embodiments of the current invention. In block 130a, a selection can be made as to whether the data in medical image of 101A should have data contralateral to the target for normal reference tissue removed prior to further processing. As the target for normal reference tissue may be asymmetrically located within the data contained within the medical image data, and the orientation of the medical image data is known a priori, this can proceed automatically, if so selected by the user (Block 130b). In block 131, a selection is made as to whether to the medical image of 101A, with or without removal of contralateral data, should be smoothed. If so, in block 132, smoothing filter is applied to medical image of block 101A, with or without removal of contralateral data, by using initial conditions of block 133. The initial conditions may include, for example, floor level, termination standard deviation, etc. In block 134, the medical image of block 101A, with or without smoothing and with or without removal of contralateral data, can be masked by a windowing function. The windowing function may, for example, crop all image voxels with intensity values below the floor value or above a ceiling level (e.g., the ceiling level may be at three times the floor value). The cropped image voxels may be assigned zero value in intensity. A homogeneity index for the masked medical image may then be calculated to ascertain the quality of the masking. If the homogeneity index is no less than a pre-determined criterion, a new floor value may be generated based on the homogeneity index, and an updated masked medical image may be iteratively provided by applying the new floor value, as discussed below.

Block 135 switches between a slice mode and a volume mode. Blocks 136 to 141 show the branch flow under the volume mode while blocks 142 to 148 show the branch flow under the slice mode. In block 136, a statistic mean and standard deviation of the volume can be calculated. In block 137, if the standard deviation is not within the input criteria from block 133, an updated masked volume may be created per block 139 according to a window of, for example, mean minus the standard deviation and mean plus twice the standard deviation. The updated masked image may feed to block 136 to calculate the corresponding statistical mean and standard deviation. If, however, the standard deviation is within the input criteria from block 133, then an eroded image may be provided in block 138 based on the masked medical image or the updated masked medical image. The eroded image may undergo further erosion until no non-zero image voxels remain. Thus, the erosion may comprise at least one iteration. The last volume of the eroded image before the number of non-zero image voxels vanishes can be utilized to calculate a spatial center of the non-zero image voxels. The spatial center may be, for example, a non-weighted centroid. Under the slice mode, data masking statistics are measured on transaxial or cross-sectional slices with the greatest number of non-zero pixels within the specified activity window. In addition, the center coordinates are generated on that same slice. Otherwise, blocks 142 to 148 under the slice mode operate in the substantially same way as blocks 136 to 141.

Thereafter, in block 149, the reference value of the volume may be generated by sampling the medical image of block 101A using image voxels having corresponding characteristic spatial locations within a pre-determined distance from the derived spatial center. For example, the distance may be 1 cm or 2 cm, etc. The derived reference value may include, for example, a statistic mean and a statistical standard deviation of image voxels having corresponding characteristic spatial locations within the pre-determined distance from the derived spatial center.

Continuing the flow chart of FIG. 1B after blocks 112 and 113, a quality assessment may be performed in block 114 on the derived normal reference value. A quality assessment may take the form of, for example, a visual check of the location from which the normal reference value has been derived, that the homogeneity of the sample is within a specified, imaging modality/protocol dependent confidence interval, etc. The purpose of an automatically derived reference value is to remove both inter-operator as well as intra-operator variability from a longitudinal analysis. If the quality assessment of an automatically generated reference value reveals that the reference value is of inferior quality, then the switch 115 will direct the flow to the manual method of block 113 of FIG. 1B. Otherwise, block 116 may calculate an individualized disease threshold 106 based on the patient specific reference value automatically derived per block 112. The disease threshold 106 may be computed, for example, according to a standard disease threshold algorithm (1.5×mean+2×standard deviation) or the variants such as the Total Lesion Glycolysis (TLG) algorithm (1.0×mean+2×standard deviation).

Turning to the detailed layout of block 107 in FIG. 1B, block 117 generates a map comprising spatial information of candidate disease tissue regions in the medical image. The spatial information may include a coordinate map. Disease objects in the medical image may be iteratively identified based on the map as discussed below.

In block 119, a ranking of the candidate disease tissue regions may be provided according to voxel intensity values of target voxels corresponding to the candidate disease tissue regions. The ranking of disease candidates may, for example, take the form of sorting, from highest value to lowest value, of candidates based on the chosen criteria for candidacy. If the voxel intensity value of the highest ranking target voxel is greater than the threshold value of block 106, a disease object may be grown around the target voxel's spatial location in the first medical image according to a user-selectable criterion. The criterion may include, for example, an absolute or fixed threshold as in PERCIST, a relative or variable threshold (e.g., percentage of max or peak value), or multi-variable threshold, etc. The disease object may be a portion of the medical image of block 101A comprising a plurality of connected image voxels. Once the disease object is identified in the medical image of block 101A; information of the spatial locations of the disease object may be subsequently extracted from map 118 according to block 122. Data encoding the spatial location of the identified disease objects may then be entered into database 124 per block 123. In block 125, database 124 may be reviewed, for example, manually for false positives in the medical image. Some normal tissue regions, for example, the heart, tend to have high metabolic activities and can be mistakenly identified as a disease object. If false negatives are identified, they can be easily removed. Thereafter, a disease assessment report 108A can be generated, as shown in FIG. 1A. In a similar fashion, disease assessment report 108B may be generated at a later observation point. The disease assessment reports at different observation times may be compared at block 109 to generate a report on disease progression or treatment response.

Baseline FDG-PET studies acquired on 29 patients participating in an Intramural Review Board (IRB) approved multi-site clinical trial for the treatment of breast cancer were analyzed to demonstrate the feasibility of the proposed computer-assisted method. For each study, the expert reader was tasked with placing a 3 cm diameter spherical Volume of Interest (VOI) in the right liver lobe region on the corresponding PET/CT images and recording both the statistical mean and the standard deviation in units of specific uptake value lean body-mass (SUL). Then, using PERCIST 1.0 methods (at both the standard and TLG calculated thresholds for disease detectability), the expert reader identified disease lesions and recorded statistical characteristics of the detected disease lesions to the best of their ability using available clinical software. For each study, the computer-assisted approach first estimated the reference value from normal hepatic tissue regions on the PET/CT images. The reference value was recorded as the statistical mean and standard deviation from a 3 cm spherical volume of interest automatically placed within the imaging study volume within the hepatic tissue region. In this feasibility study, the correctness, or suitability, of the automatically selected hepatic tissue region was confirmed by a trained medical imaging expert in this trial study. The disease threshold were then computed per the standard or TLG algorithm under PERCIST 1.0 framework.

Figure 2:
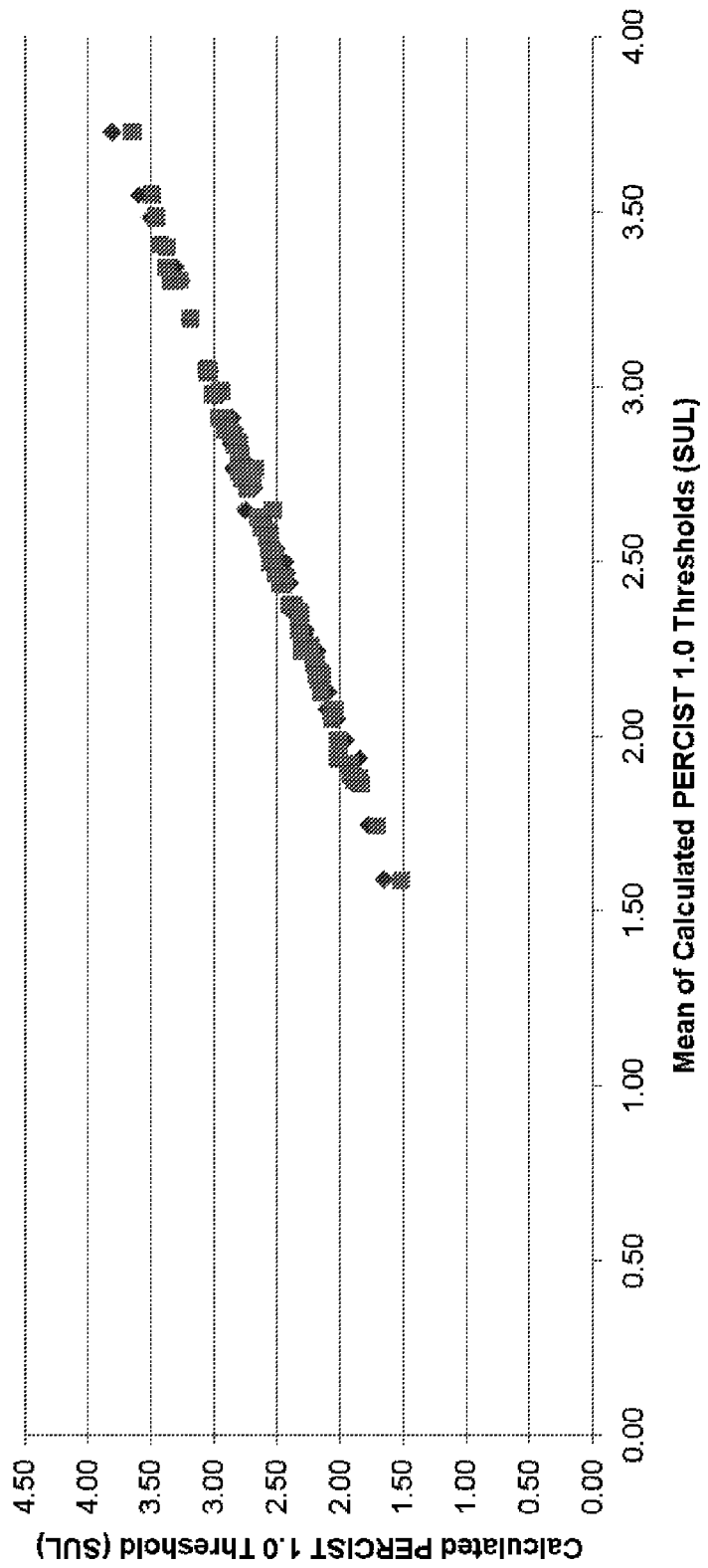
FIG. 2 compares example results of calculated thresholds from a manual method and an automated method according to some embodiments of the current invention.

FIG. 2 compares example results of the calculated disease thresholds from a manual method and an automated method according to some embodiments of the current invention.

Figure 3A:
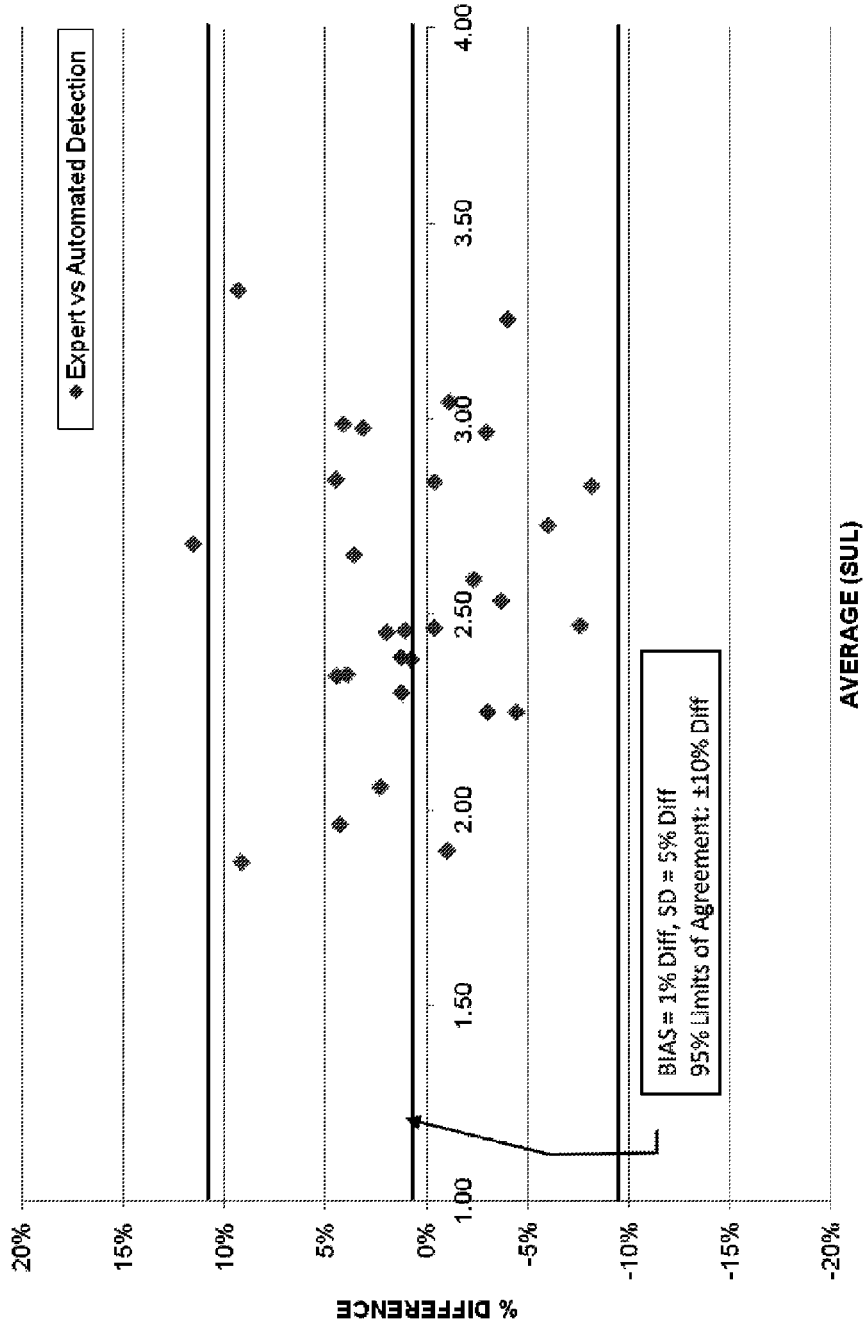
FIG. 3A compares the measured PERCIST 1.0 disease thresholds per the standard algorithm between expert and automated detection according to some embodiments of the current invention.

FIG. 3A compares the measured PERCIST 1.0 disease thresholds per the standard algorithm between expert and automated detection according to some embodiments of the current invention. For the standard PERCIST threshold, the statistical difference between the expert reader and the automated method is 0.02±0.13 SUL, with a p-value of 0.46, indicating that the difference between the expert reader and the automated method is not statistically significant.

Figure 3B:
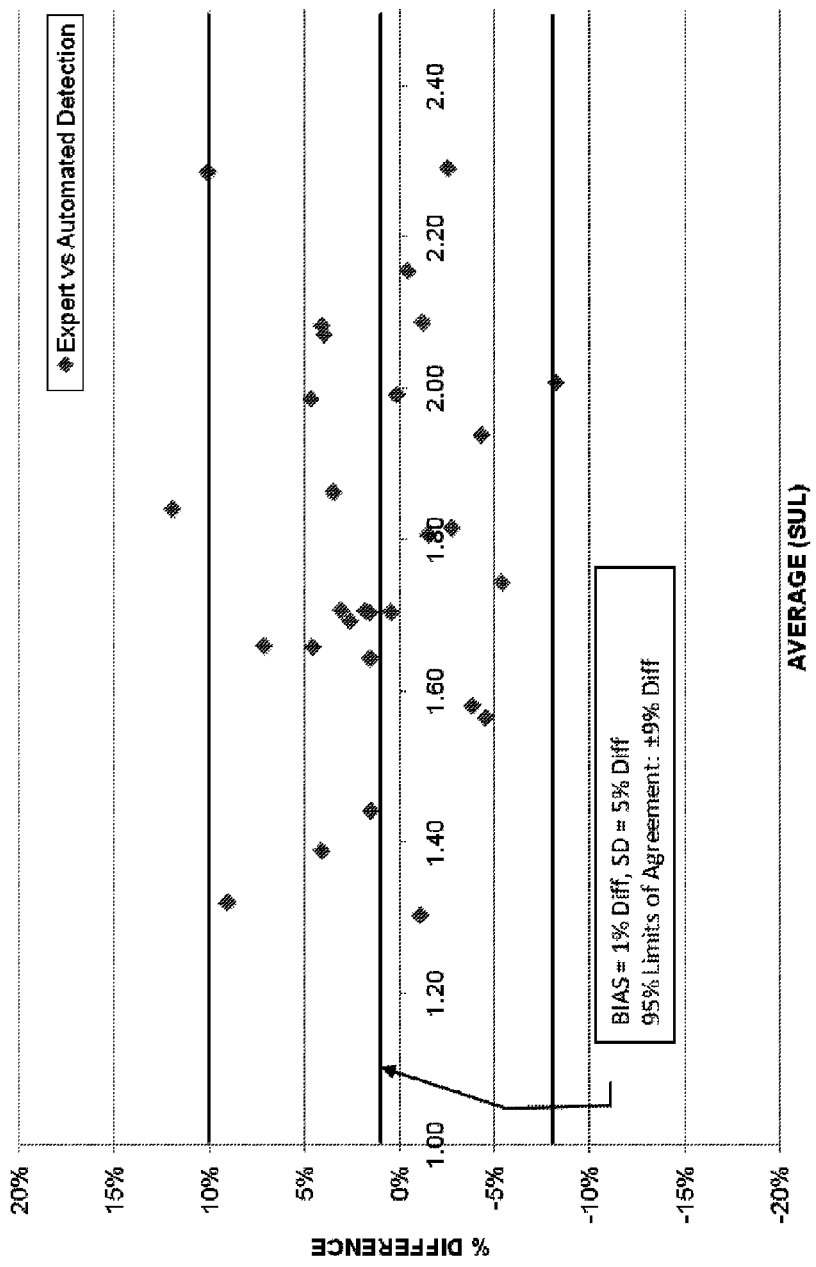
FIG. 3B compares the measured PERCIST 1.0 disease thresholds per the TLG algorithm between expert and automated detection according to some embodiments of the current invention.

FIG. 3B compares the measured PERCIST 1.0 disease thresholds per the TLG algorithm between expert and automated detection according to some embodiments of the current invention. For the TLG PERCIST threshold, the statistical difference between the expert reader and the automated method is 0.02±0.09 SUL, with a p-value of 0.15, again indicating that the difference between the expert reader and the automated method is not statistically significant.

FIG. 4A tabulates the summary outcome from the expert and automated detection using the standard disease threshold algorithm according to some embodiments of the current invention. PEAK refers to the local maxima in a smoothed image while MAX refers to the local maxima in an unsmoothed image.

FIG. 4B tabulates the summary outcome from the expert and automated detection using the TLG disease threshold algorithm according to some embodiments of the current invention. Using the PERCIST 1.0 preferred metric of SUL-PEAK, disease lesion was detected in over 93% of the cases (27 of 29) per the manual method (by expert readers) and the computer-assisted method according to some embodiments of the current invention. In general, the computer-assisted method demonstrates a high concordance with the expert readers in detection outcome.

FIG. 4C compares the summary outcome from the expert and automated detection using the standard and TLG disease threshold algorithms according to some embodiments of the current invention. The TLG disease threshold may be superior to the standard threshold for disease detection in certain disease types, such as breast cancer. However, in other disease types or when other metrics (such as percentage of SUV decline) are being sought, the TLG threshold may not be as superior as demonstrated in FIGS. 4A-4C.

FIG. 5A shows an example detection of disease region in one original medical image of using the standard and the TLG disease thresholds determined according to some embodiments of the current invention. The detected lesions based on the two thresholds were well-matched.

Figure 5B:
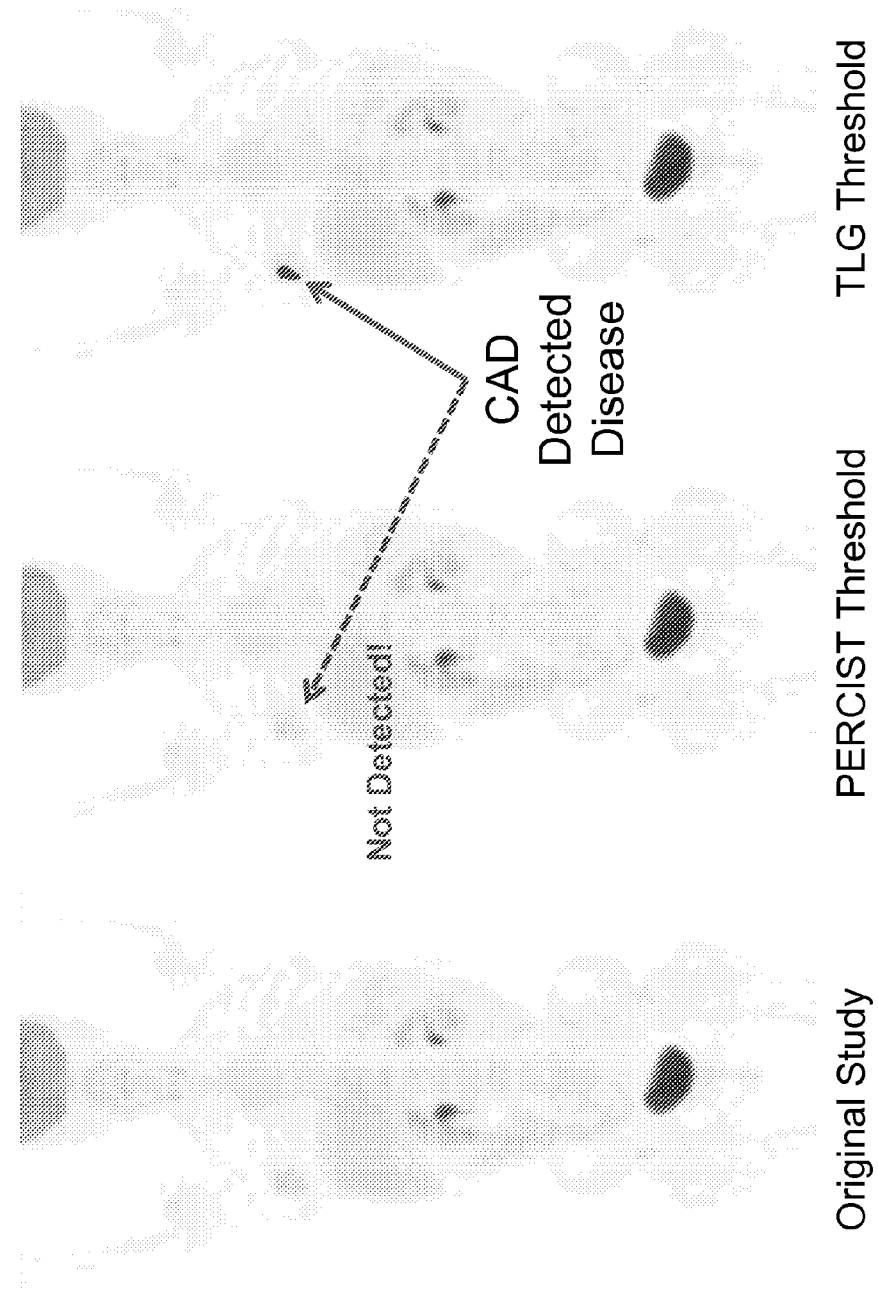
FIG. 5B shows another example detection of disease region in one original medical image of using the standard and the TLG disease thresholds determined according to some embodiments of the current invention.

FIG. 5B shows another example detection of disease region in one original medical image of using the standard and the TLG disease thresholds determined according to some embodiments of the current invention. More lesions were detected according to the TLG threshold, indicating a potential superiority in sensitivity associated with the TLG threshold. The TLG may be more sensitive, but may be less specific. The design choice may be to use a phenotype specific threshold. These studies are examples of the "user-selectable" feature of this framework.

In this application, a computer-assisted method has been proposed for longitudinally measuring a patient's condition over time. This computer-assisted method can be objectively implemented by different users in a multi-center environment. Specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A computer-implemented method for image processing, the method comprising:
   receiving a first medical image from a data storage device, said first medical image comprising a plurality of image voxels and representing a plurality of tissue regions of a subject;
   automatically determining a reference value based on said first medical image, said reference value capable of providing a range of background level of voxel intensity values within at least one non-disease tissue region of said subject;
   generating a disease threshold based on the reference value;
   identifying portions of the medical image corresponding to disease-tissue regions according to said disease threshold, each of said portions comprising a plurality of connected image voxels in said medical image; and
   entering data encoding said disease-tissue regions into a database for subsequent comparisons,
   wherein said identifying portions of the medical image comprises:
   generating a map comprising spatial locations of candidate disease tissue regions in the medical image; and
   iteratively identifying disease objects in the medical image based on said map, and
   wherein said iteratively identifying comprises:
   providing a ranking of said candidate disease tissue regions according to voxel intensity values of target voxels corresponding to said candidate disease tissue regions; and
   if the voxel intensity value of the highest ranking target voxel is greater than said disease threshold,
   growing a disease object around the target voxel's spatial location in the first medical image according to a user-selectable criterion;
   identifying a portion of the first medical image at the spatial locations of said disease object, said portion comprising a plurality of connected image voxels;
   subsequently remove spatial locations of said disease object from said map.

2. A computer-implemented method of claim 1, wherein said automatically determining comprises:
   providing a masked medical image by cropping said first medical image based on a pre-determined initial windowing value;
   calculating an homogeneity index for said masked medical image; and
   if said homogeneity index is no less than a pre-determined criterion, generating a new windowing value based on said homogeneity index, and iteratively providing an updated masked medical image by applying said new windowing value.

3. A computer-implemented method of claim 2, wherein said automatically determining further comprises:
   providing an eroded image based on the masked medical image or the updated masked medical image, said eroded image comprising non-zero image voxels;
   calculating a spatial location corresponding to a center of said non-zero image voxels; and
   generating said reference value by sampling said first medical image based on image voxels with corresponding characteristic spatial locations within a pre-determined distance from said center.

4. A computer-implemented method of claim 3, wherein said center corresponds to a non-weighted centroid.

5. A computer-implemented method of claim 3, wherein said reference value comprises: a statistical mean, a statistical standard deviation, or a confidence interval.

6. A computer-implemented method of claim 3, wherein said eroded image is obtained after at least one iterations.

7. A computer-implemented method of claim 2,
   wherein said pre-determined initial windowing value comprises a floor level and a ceiling level, and
   wherein said cropping causes zero values to be assigned to image voxels with intensity values lower than said floor level or higher than said ceiling level.

8. A computer-implemented method of claim 2, wherein said homogeneity index comprises a statistical mean and a statistical standard deviation based on image voxels in the masked image having non-zero intensity values.

9. A computer-implemented method of claim 1, wherein said disease tissue regions comprise one of: a tumor, a neoplasia, a hyperplasia, or a dysplasia, a neurodegenerative disorder condition.

10. A computer-implemented method of claim 1, wherein said identifying portions of the medical image further comprises:
reviewing said disease tissue regions identified in the medical image to remove at least one false positive.

11. A computer-implemented method of claim 1, wherein said user-selectable criterion comprises one of: an absolute threshold or a relative threshold.

12. A method of claim 1, further comprising:
receiving a second medical image from said data storage device or a different data storage device, said second medical image comprising a plurality of image voxels and representing a plurality of tissue regions of a subject;
automatically determining a second reference value based on said second medical image; generating a second disease threshold based on said second reference value;
identifying portions of the second medical image corresponding to disease tissue regions according to said second disease threshold; and
entering data encoding said disease tissue regions into said database.

13. A computer-implemented method of claim 12, further comprising:
monitoring a disease tissue region of said subject by comparing database entries corresponding to said disease tissue region based on said first medical image and said second medical image.

14. A computer-implemented method of claim 12, further comprising:
generating an assessment report comprising information showing a progression of said disease tissue region or a treatment response of said disease tissue region.

15. A computer-implemented method of claim 14, wherein said treatment comprises one of: a radiation treatment, a chemotherapy, an high-intensity focused ultrasound (HIFU) treatment, a radio-frequency (RF) ablation treatment, a laser ablation treatment, or an oral-dose treatment.

16. A computer-implemented method of claim 1, wherein said subject comprises one of: a human patient, or an animal patient.

17. A non-transitory computer-readable medium, comprising software instructions, when executed by a computer, causes the computer to implement the method of claim 1.

* * * * *